United States Patent
Hsieh et al.

(10) Patent No.: US 6,979,314 B2
(45) Date of Patent: Dec. 27, 2005

(54) SAFETY SYRINGE

(75) Inventors: Hsin-Po Hsieh, Chian-Hwa Hsien (TW); Chi-Zer Ho, Taipei (TW); Shih-Chun Wang, Chia-Yi (TW)

(73) Assignee: Syriteck Medical Devices Co., Ltd., Taichung (TW)

( * ) Notice: Subject to any disclaimer, the term of this patent is extended or adjusted under 35 U.S.C. 154(b) by 233 days.

(21) Appl. No.: 10/683,433

(22) Filed: Oct. 14, 2003

(65) Prior Publication Data

US 2005/0080382 A1    Apr. 14, 2005

(51) Int. Cl.[7] .............................................. A61M 5/00
(52) U.S. Cl. ........................ 604/110; 604/218; 128/919
(58) Field of Search ........................ 604/110, 187, 192, 604/198, 218, 222, 221; 128/919

(56) References Cited

U.S. PATENT DOCUMENTS

| | | | | |
|---|---|---|---|---|
| 4,923,443 A | * | 5/1990 | Greenwood et al. | 604/110 |
| 5,215,536 A | * | 6/1993 | Lampropoulos et al. | 604/220 |
| 5,401,246 A | * | 3/1995 | Mazur et al. | 604/110 |
| 5,462,531 A | * | 10/1995 | Novacek et al. | 604/110 |
| 5,520,649 A | * | 5/1996 | Novacek et al. | 604/110 |
| 5,820,605 A | * | 10/1998 | Zdeb et al. | 604/195 |
| 5,968,019 A | * | 10/1999 | Lee | 604/195 |
| 6,344,031 B1 | * | 2/2002 | Novacek et al. | 604/195 |
| 6,706,015 B2 | * | 3/2004 | Bang | 604/110 |
| 2003/0212366 A1 | * | 11/2003 | Bang | 604/196 |
| 2004/0082911 A1 | * | 4/2004 | Tiu et al. | 604/110 |

* cited by examiner

Primary Examiner—LoAn H. Thanh
(74) Attorney, Agent, or Firm—Rosenberg, Klein & Lee

(57) ABSTRACT

A safety syringe has a hollow barrel, a plunger, a connector, a plug and a needle hub. The plunger has a protrusion extended from the plunger and along a longitudinal axis of the plunger. The connector is mounted around the protrusion of the plunger. Multiple limit stubs and multiple curved limit channels communicating with a corresponding notch with an inclined side-wall are respectively formed on the connector and a connecting chamber in a connecting tube of the needle hub. When the plunger is being pushed towards the needle hub, the multiple limit stubs respectively pass through the corresponding curved limit channel and are contained in the corresponding notch. The inclined side-wall of the notch will stably connect the limit stub so the plunger can stably retract the needle hub in the hollow barrel.

6 Claims, 6 Drawing Sheets

SAFETY SYRINGE

BACKGROUND OF THE INVENTION

1. Field of the Invention

The present invention relates to a syringe, and more particularly to a safety syringe that can stably retract the used needle.

2. Description of Related Art

A conventional syringe has a hollow barrel, a plunger and a needle hub. Due to possible exposure to contagious diseases, the needle of the syringe and even the hollow barrel and the plunger, should not be used again and should be discarded immediately after use. Also, to keep nurses, doctors or health workers who deal with discarded syringes from getting injured or infected by used needles, a safety syringe is needed. In particular, manufacturers have focused on syringes with retractable needles so that once the syringe has been used, the contaminated needle is entirely housed within the barrel whereby the chance of infection through accidental pricking is eliminated.

A conventional safety syringe disclosed in Taiwan Pat. No. 356013 and comprises a hollow barrel, a plunger and a needle hub. The plunger has a connector formed on one end of the plunger to connect with the needle hub. The connector has a protrusion. The needle hub comprises a chamber and an annular rib. The chamber has a distal closed end and a proximal open end. The annular rib extends radially inward from the proximal open end of the chamber. The protrusion of the connector can be clipped by the annular rib of the needle hub to connect the plunger and the needle hub together. When the plunger is pushed to the needle hub, the connector of the plunger is pressed by the annular rib of the needle hub and then contained in the needle hub, whereafter pulling the plunger will retract the needle hub into the hollow barrel.

However, the connector of the plunger and the needle hub often separate from each other after the plunger is pulled back to retract the needle hub. When the protrusion of the connector is pulled toward the hollow barrel, since the needle hub is elastically connected to the annular rib of the needle hub, the elastic connection often slips to let the protrusion of the connector separate from the needle hub. If the annular rib of the needle hub is produced small in order to prevent from the protrusion of the connector separating from the needle hub, the protrusion of the connector will be difficult to mount in the chamber of the needle hub when trying to engage the plunger with the needle hub.

SUMMARY OF THE INVENTION

The main objective of the present invention is to provide a safety syringe that can have reliable engagement and separation between a plunger and a needle hub. To achieve the objective, a safety syringe in accordance with the present invention comprises a hollow barrel, a plunger, a connector, a plug and a needle hub. The plunger is slidably mounted in the hollow barrel, and has a neck to mount the plug and a protrusion extended from the plunger and along a longitudinal axis of the neck. The connector is mounted around the protrusion of the plunger. The needle hub is mounted in one end of the hollow barrel and comprises a connecting tube and a needle. Multiple limit stubs and multiple curved limit channels communicated with a corresponding notch with a second inclined side wall are respectively formed on the connector and in the connecting chamber of the needle hub. When the plunger is being pushed toward the needle hub, the multiple limit stubs respectively pass through the corresponding curved limit channel and are contained in the corresponding notch. The second inclined side wall of the notch will stably connect the limit stub so the plunger can stably retract the needle hub in the hollow barrel.

Further benefits and advantages of the present invention will become apparent after a careful reading of the detailed description with appropriate reference to the accompanying drawings.

DETAILED DESCRIPTION OF THE INVENTION

Figure 1:
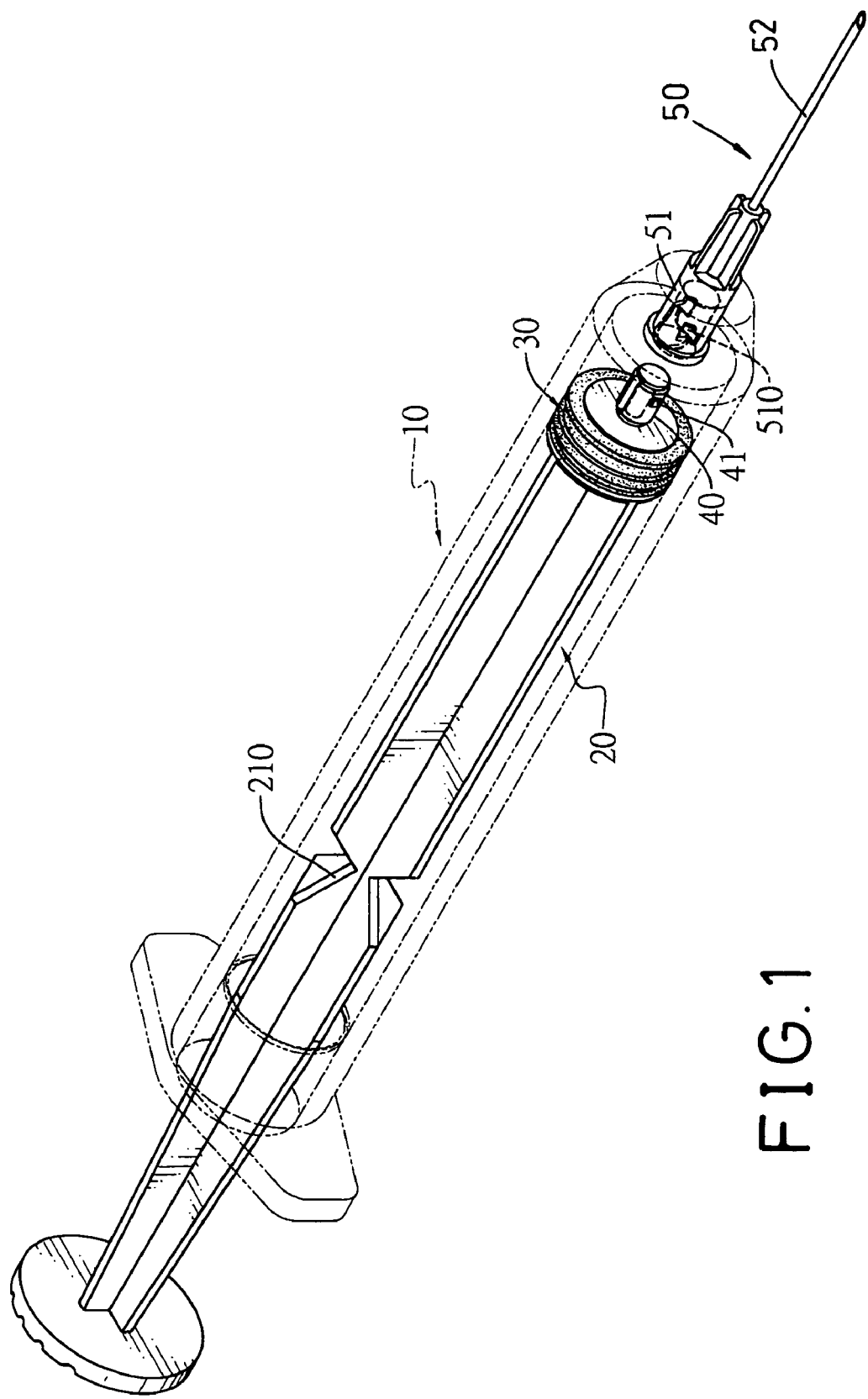
FIG. 1 is a perspective view of a safety syringe in accordance with the present invention.
Figure 2:
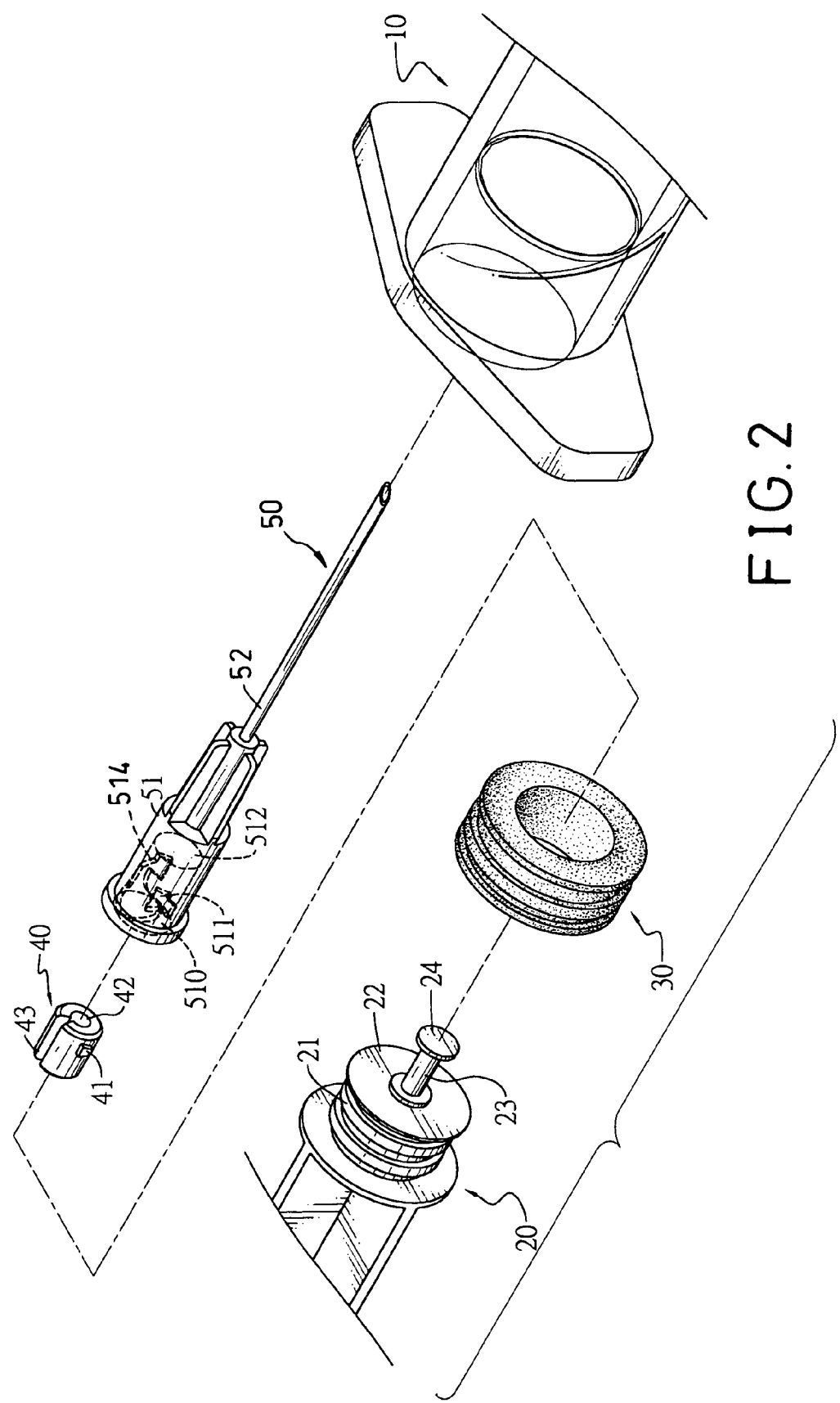
FIG. 2 is an exploded perspective view of the safety syringe in FIG. 1.
Figure 6:
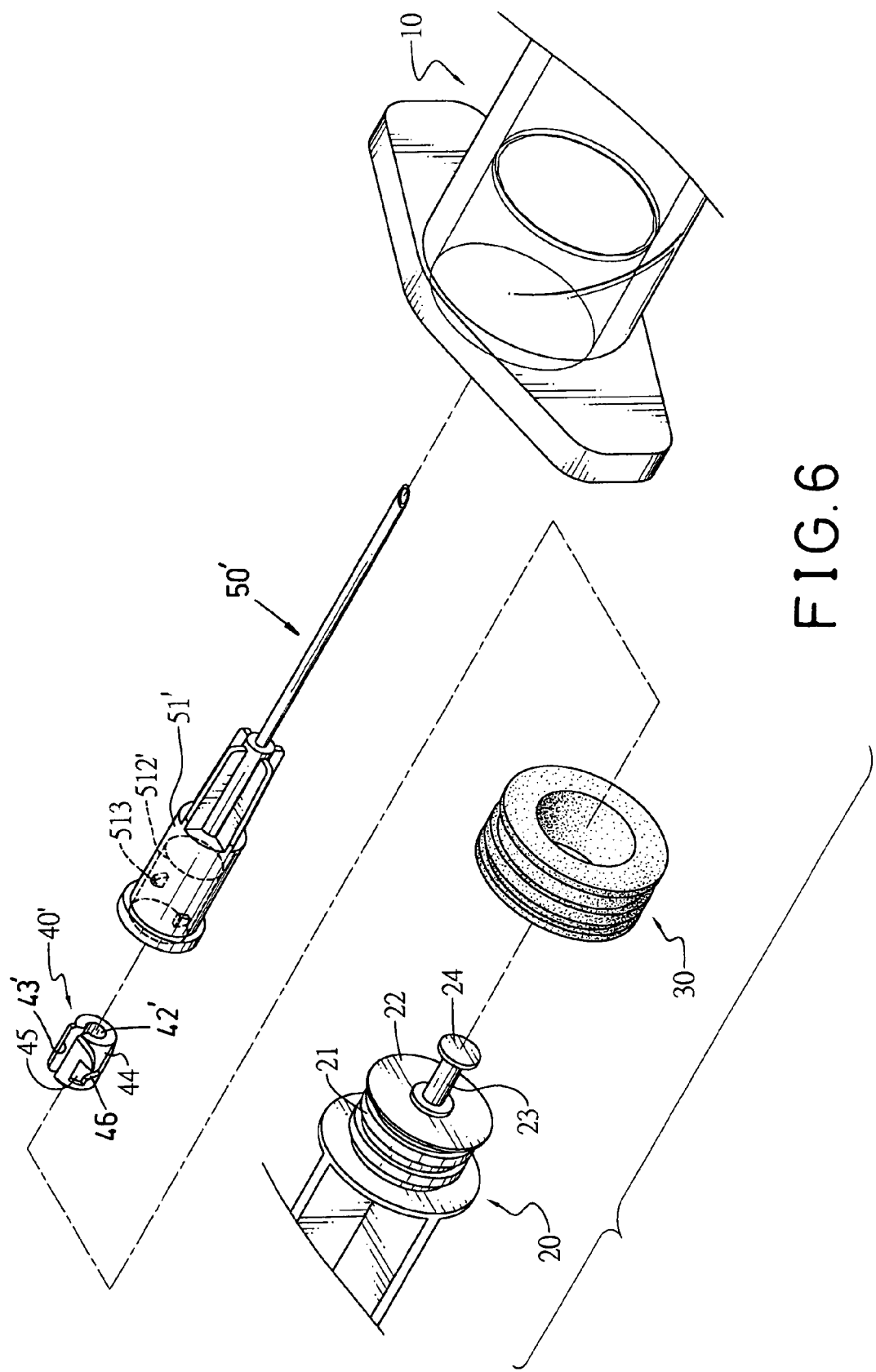
FIG. 6 is an exploded perspective view of a second embodiment of a safety syringe in accordance with the present invention.

With reference to FIGS. 1, 2 and 6, a safety syringe in accordance with the present invention comprises a hollow barrel (10), a plunger (20), a plug (30), a connector (40,40'), an engaging device (not numbered) and a needle hub (50, 50').

The hollow barrel (10) is cylindrical and has a proximal open end (not numbered), a distal open end (not numbered), a lip (not numbered) and an annular flange (not numbered). The lip extends radially inward from the proximal open end of the hollow barrel (10) so the proximal open end is smaller than the distal open end. The annular flange extends radially out from the distal open end of the hollow barrel (10).

The plunger (20) has a distal end (not numbered), a proximal end (not numbered), a V-shaped groove (210), a neck (21), a first positive limit (22), a protrusion (23) and a second positive limit (24), and is slidably mounted inside the hollow barrel (10). The neck (21) is formed integrally and extends from the proximal end of the plunger (20), and has a distal end (not numbered), a proximal end (not numbered) and a longitudinal axis (not numbered). The first positive limit (22) is circular and attached to the proximal end of the neck (21). The protrusion (23) is extended from the first positive limit (22) and along the longitudinal axis of the neck (21), and has a distal end (not numbered) and a proximal end (not numbered). The second positive limit (24) is circular and attached to the proximal end of the protrusion (23). The V-shaped groove (210) is defined radially in the plunger (20).

The plug (30) is mounted around the neck (21) on the plunger (20).

The connector (40,40') is cylindrical and rotatively mounted around the protrusion (23) of the plunger (20), and has a side-wall (not numbered), a longitudinal axis (not numbered), a through hole (42,42') and a groove (43,43'). The through hole (42,42') is formed along the longitudinal axis of the connector (40). The groove (43,43') is formed in the side-wall and extends parallel to the longitudinal axis of the connector (40,40'), and communicates with the through hole (42,42') of the connector (40,40').

Figure 3:
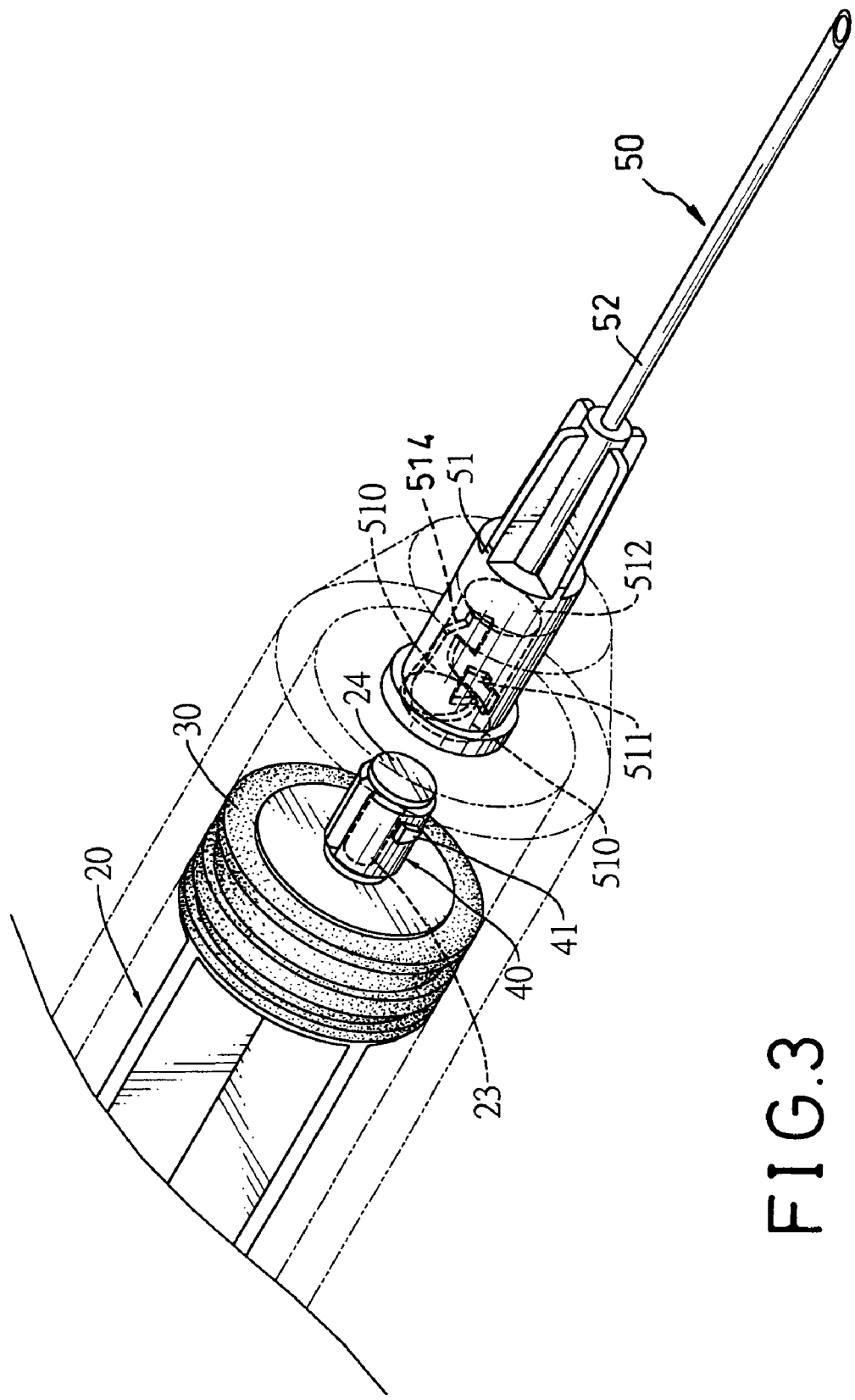
FIG. 3 is a perspective view of the partial safety syringe in FIG. 1.

With further reference to FIG. 3, the needle hub (50,50') is mounted in the proximal open end of the hollow barrel (10) and has a connecting tube (51,51') and a needle (52). The connecting tube (51,51') has a distal end (not numbered), a proximal end (not numbered) and a connecting chamber (512,512'). The connecting chamber (512,512') is formed in the distal end of the connecting tube (51,51') and has a proximal open end (not numbered), a distal end (not numbered) and an inner surface (not numbered). The connecting chamber (512,512') has a radius larger than that of the connector (40,40'). The needle (52) is attached to the proximal end of the connecting tube (51,51') and has a central passage (not shown).

The engaging device is formed between the connector (40,40') and the connecting chamber (512,512') of the needle hub (50,50'). The engaging device connects the connector (40,40') and the connecting chamber (512,512') of the needle hub (50,50') together when the connector (40,40') is inserted into the connecting chamber (512,512'). In a first embodiment, the engaging device comprises multiple limit stubs (41), multiple curved limit channels (510) and multiple notches (511). The multiple limit stubs (41) protrude from the side-wall of the connector (40). The multiple curved limit channels (510) are defined in the inner surface and respectively correspond to a limit stub (41), and each opens from the proximal open end of the connecting chamber (512). The multiple curved limit channels (510) are trumpet shaped and each curved limit channel has a first inclined side wall (514). The multiple notches (511) are formed in the inner surface and respectively communicate with a corresponding curved limit channel (510), and have a second inclined side wall (not numbered). The first inclined side wall (514) and the second inclined side wall are formed oppositely and the first inclined side wall (514) is formed near the notch (511). The multiple notches (511) of the connecting tube (51) can respectively contain a corresponding limit stub (41) and each notch (511) is larger than the corresponded limit stub (41).

With reference to FIG. 6, a second embodiment of the engaging device comprises multiple curved limit channels (44), multiple notches (45) and multiple limit stubs (513). The multiple curved limit channels (44) are defined in the side-wall of the connector (40') and open toward the needle hub (50). The curved limit channels (44) of the connector (40') are trumpet shaped and has a first inclined side wall (46). The multiple notches (45) are formed in the side-wall of the connector (40) and respectively communicate with a corresponding curved limit channel (44), and each notch (45) has a second inclined side wall (not numbered). The first inclined side wall (46) and the second inclined side wall are formed oppositely and the first inclined side wall (46) is formed near the notch (45). The multiple limit stubs (513) protrude from the inner surface of the connecting chamber (512') and correspond to the respective curved limit channel (44) of the connector (40'). The multiple limit stubs (513) of the connecting tube (51') can be respectively contained in the corresponding notch (45) of the connector (40'). Each limit stub (513) is smaller than the corresponding curved limit channel (44) of the connector (40').

Figure 4:
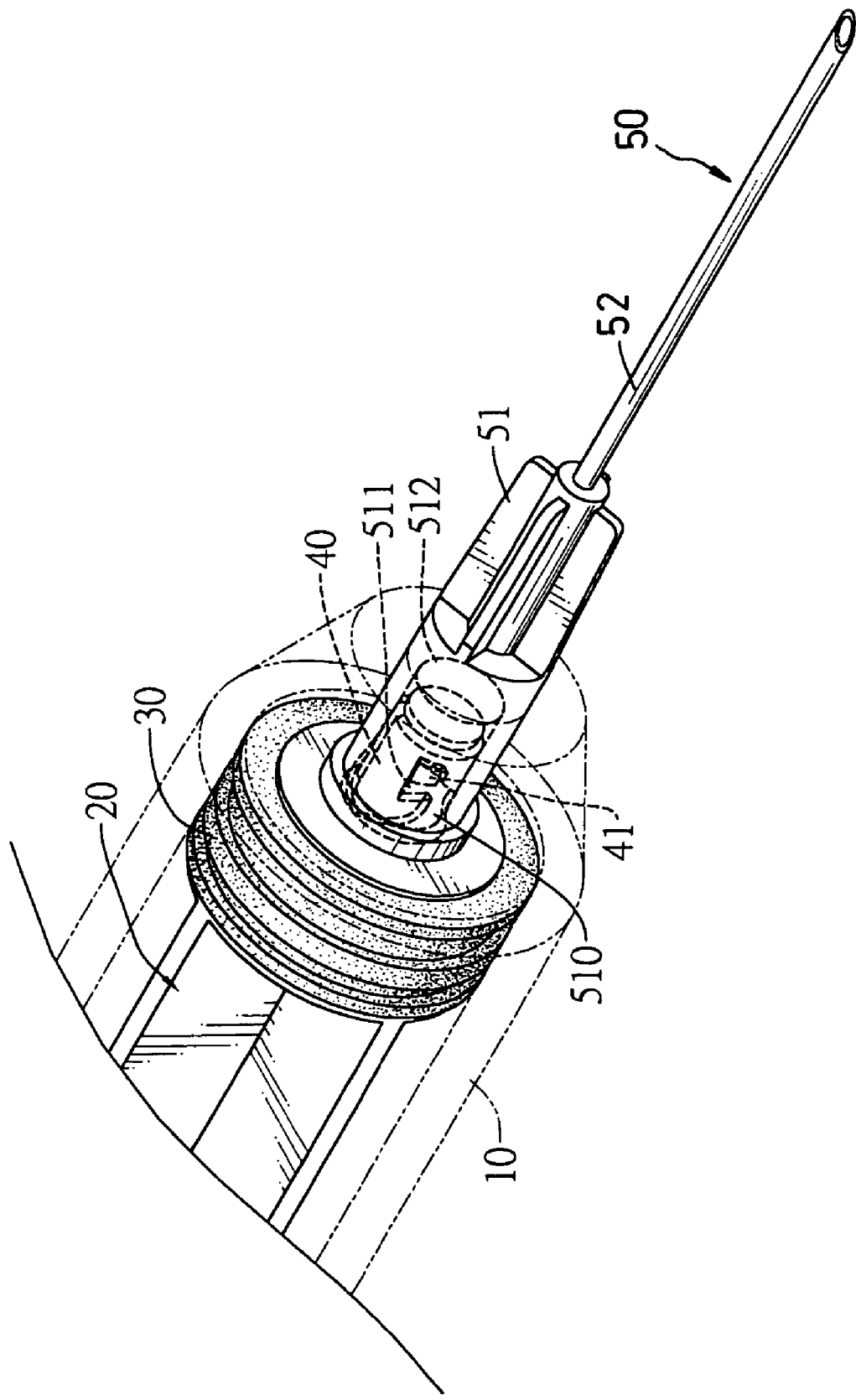
FIG. 4 is a perspective view of the partial safety syringe in FIG. 1 showing multiple limit stubs on a connector respectively mounted into a corresponding recess inside a connecting tube.

With further reference to FIGS. 3 and 4, the safety syringe is used and the plunger (20) is pushed toward the proximal open end of the hollow barrel (10) to engage with and retract the needle hub (50). The connector (40) will rotate to a suitable location and let the multiple limit stubs (41) of the connector (40) respectively move along the corresponding curved limit channel (510) and the first inclined side wall such that each limit stub (41) is mounted into the corresponding notch (511). Thus, the plunger (20) and the needle hub (50) are connected together. Pulling back the plunger (20) into the hollow barrel (10) will let each limit stub (41) wedge with the second inclined side wall of the notch (511) and stably connect the plunger (20) and the needle hub (50). Continuously pulling the plunger (20) will retract the needle hub (50) into the hollow barrel (10).

Figure 5:
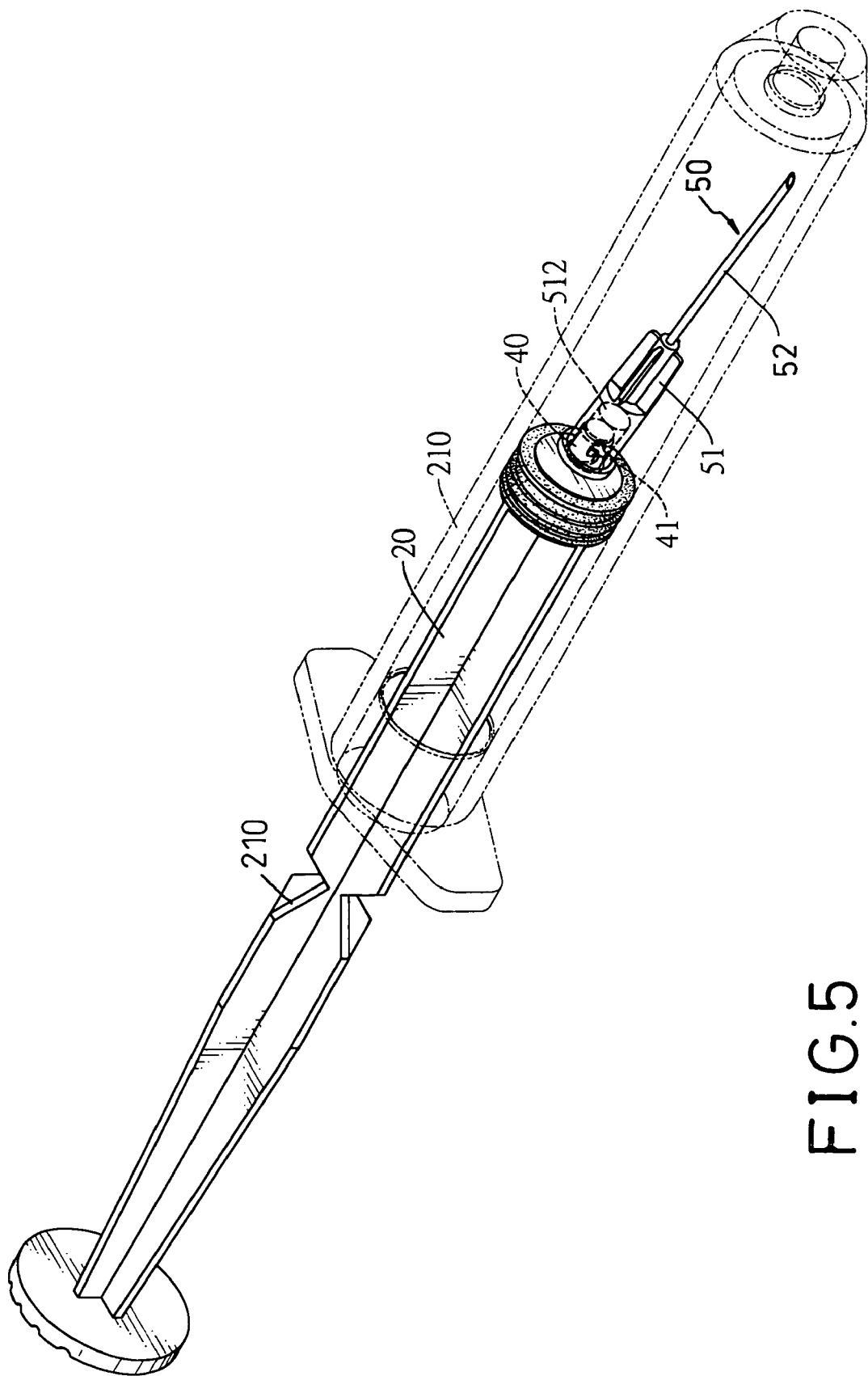
FIG. 5 is a perspective view of the safety syringe in FIG. 1 showing the needle hub retracted back into a hollow barrel.

With further reference to FIG. 5, pulling the plunger (20) toward the distal open end of the hollow barrel (10) will pull the needle hub (50) back into the hollow barrel (10). Since the radius of the connecting chamber (512) in the needle hub (50) is larger than that of the connector (40), the needle (52) will incline by gravity and use the limit stub (41) as a fulcrum. The needle hub (50) cannot be pushed out from proximal open end of the hollow barrel (10). After the V-shaped groove (210) of the plunger (20) exits the hollow barrel (10), the V-shaped groove (210) of the plunger (20) permits the protruding portion of the plunger (20) to be snapped off whereby the needle hub (50) is retained inside the hollow barrel (10).

In the second embodiment of the safety syringe, with reference to FIG. 6, the connector (40') will rotate to a suitable location and let the multiple limit stubs (41) of the connecting chamber (512') in the needle hub (50') respectively move along the corresponding curved limit channel (44) and be mounted into the corresponding notch (45). The multiple limit stubs (41) will respectively wedge to the corresponding second inclined side wall of the notch (45). Thus, the plunger (20) and the needle hub (50') are connected together stably.

The safety syringe in accordance with the present invention can let the plunger (20) connect with the needle hub (50,50') stably. After the safety syringe has been used to treat a patient, the plunger (20) can connect with the needle hub (50,50') to let the needle hub (50,50') retract back in the hollow barrel (10).

Although the invention has been explained in relation to its preferred embodiment, many other possible modifications and variations can be made without departing from the spirit and scope of the invention as hereinafter claimed is to be understood.

What is claimed is:

1. A safety syringe comprising:
   a hollow barrel having
      a proximal open end; and
      a distal open end;
   a plunger slidably mounted inside the hollow barrel and having
      a distal end;
      a proximal end;
      a neck formed integrally and extending from the proximal end of the plunger, and having a distal end, a proximal end and a longitudinal axis;
      a first positive limit attached to the proximal end of the neck;
      a protrusion extended from the first positive limit and along the longitudinal axis of the neck, and having a distal end and a proximal end; and
      a second positive limit attached to the proximal end of the protrusion;
   a plug mounted around the neck on the plunger;
   a cylindrical connector rotatively mounted around the protrusion of the plunger, and having a side-wall;
a longitudinal axis;
a through hole formed along the longitudinal axis of the connector; and
a groove formed in the side-wall and parallel to the longitudinal axis of the connector, and communicating with the through hole of the connector;
a needle hub mounted in the proximal open end of the hollow barrel and having
a connecting tube having
a distal end;
a proximal end; and
a connecting chamber formed in the distal end of the connecting tube and having a proximal open end, a distal end and an inner surface, wherein the connecting chamber has a radius larger than that of the connector; and
a needle attached to the proximal end of the connecting tube and having a central passage; and
an engaging device formed between the connector and the connecting chamber of the needle hub and connected the connector and the connecting chamber of the needle hub together when the connector is inserted in to the connecting chamber, and comprising
multiple limit stubs;
multiple curved limit channels each corresponding to one of the limit stubs and having a first inclined side wall; and
multiple notches each communicating with one of the curved limit channels and having a second inclined side wall formed opposite to the first inclined side wall on a corresponding one of the curved limit channels, and the first inclined side wall formed near the corresponding notch, wherein each notch is larger than the corresponding limit stub and each limit stub wedges against the second inclined side wall of the corresponding notch when the connector is inserted into the connecting chamber.

2. The safety syringe as claimed in claim 1, wherein the push rod further comprises a V-shape groove defined radially in the push rod.

3. The safety syringe as claimed in claim 1, wherein
the multiple limit stubs protrudes from the side-wall of the connector;
the multiple curved limit channels are defined in the inner surface and opened from the proximal open end of the connecting chamber; and
the multiple notches are formed in the inner surface of the connecting chamber.

4. The safety syringe as claimed in claim 3, wherein the push rod further comprises a V-shape groove defined radially in the push rod.

5. The safety syringe as claimed in claim 1, wherein
the multiple curved limit channels are defined in the side-wall of the connector and open toward the needle hub;
the multiple notches are formed in the side-wall of the connector; and the multiple limit stubs are protruded from the inner surface of the connecting chamber.

6. The safety syringe as claimed in claim 5, wherein the push rod further comprises a V-shape groove defined radially in the push rod.

* * * * *